US011219468B1

United States Patent
Diaz-Chiosa et al.

(10) Patent No.: US 11,219,468 B1
(45) Date of Patent: Jan. 11, 2022

(54) TROCAR ASSEMBLY WITH ANTIMICROBIAL SKIRT

(71) Applicant: Covidien LP, Mansfield, MA (US)

(72) Inventors: Olesea Diaz-Chiosa, Naugatuck, CT (US); Russell V. Pribanic, Roxbury, CT (US); David A. Nicholas, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/012,212

(22) Filed: Sep. 4, 2020

(51) Int. Cl.
*A61B 17/34* (2006.01)
*A61L 24/04* (2006.01)
*A61B 17/00* (2006.01)
*C09J 4/00* (2006.01)

(52) U.S. Cl.
CPC ...... *A61B 17/3496* (2013.01); *A61B 17/3423* (2013.01); *A61B 17/3462* (2013.01); *A61L 24/046* (2013.01); *C09J 4/00* (2013.01); *A61B 2017/0065* (2013.01); *A61B 2017/00637* (2013.01); *A61B 2017/00862* (2013.01); *A61B 2017/00889* (2013.01); *A61B 2017/3435* (2013.01)

(58) Field of Classification Search
CPC ...... A61B 17/3496; A61B 2017/00637; A61B 2017/3435; A61B 2017/0065; A61B 2017/00889; A61B 2017/00862; A61B 17/3462; A61B 1/00151; A61B 1/312; A61B 17/3423; A61B 17/00491; A61B 17/085; A61B 17/34; A61B 17/3421; A61B 46/27; A61M 25/0119; A61M 25/0062; A61M 25/0017

USPC ................................................ 606/108, 130
See application file for complete search history.

(56) References Cited

U.S. PATENT DOCUMENTS

| 5,603,702 | A | 2/1997 | Smith et al. |
| 5,807,338 | A | 9/1998 | Smith et al. |
| 6,059,816 | A | 5/2000 | Moenning |
| 7,963,912 | B2 | 6/2011 | Zwolinski et al. |
| 8,070,730 | B2 | 12/2011 | Rockrohr |
| 8,419,762 | B2 | 4/2013 | Delsman |
| 8,828,023 | B2 | 9/2014 | Neff et al. |
| 9,510,925 | B2 * | 12/2016 | Hotter ............... A61F 2/0063 |
| 9,662,115 | B2 * | 5/2017 | Prior ............... A61B 17/0218 |
| 2013/0150828 | A1 | 6/2013 | Conway |
| 2015/0045623 | A1 | 2/2015 | Fischvogt |
| 2015/0142045 | A1 * | 5/2015 | Bacich ............... A61F 2/0027 606/193 |

FOREIGN PATENT DOCUMENTS

| DE | 202004016749 U1 | 1/2005 |
| WO | 2016025132 A1 | 2/2016 |

\* cited by examiner

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A trocar assembly includes a housing, an elongated cannula extending from the housing to an insertion tip, and skirt. The skirt has a leading end portion and a trailing end portion. The leading end portion is secured to the insertion tip. The skirt has an outer surface supporting an antimicrobial material and an inner surface supporting a medical adhesive material.

20 Claims, 4 Drawing Sheets

TROCAR ASSEMBLY WITH ANTIMICROBIAL SKIRT

TECHNICAL FIELD

This disclosure relates generally to surgical instruments, and in particular, to trocars for use during a minimally invasive surgical procedure.

BACKGROUND

In laparoscopic surgery, a clinician may use five or more trocars ranging from 5 mm to 15 mm in diameter. These trocars are strategically positioned in a patient to enable triangulation of surgical instruments for maximum reach and access. The size of the diameter of each trocar is directly related to the risk of herniation, patient pain, and/or surgical site incision infections (SSI). The chances of a patient developing an SSI post-surgery are about 1% to 3%. These infections can be superficial infections (skin only) or more serious infections that involve tissue under the skin, organs, or implanted material. SSI have been shown to increase mortality, readmission rate, length of stay, and patient costs. Such infections are more likely to occur after surgery on parts of the body that harbor a significant number of germs: intestines, colon, etc. Accordingly, it remains important to retain a sterile environment when introducing surgical instruments into the patient and when extracting tissue from the patient.

SUMMARY

In accordance with one aspect, this disclosure is directed to a trocar assembly. The trocar assembly includes a housing, an elongated cannula extending from the housing to an insertion tip, and a skirt. The skirt has a leading end portion and a trailing end portion. The leading end portion is secured to the insertion tip. The skirt has an outer surface supporting an antimicrobial material and an inner surface supporting a medical adhesive material.

In aspects, the medical adhesive material may include cyanoacrylate.

In aspects, the skirt may be is flexible.

In aspects, the trailing end portion of the skirt may be a free end.

In aspects, the skirt may be positioned to move between a first position and a second position. In the second position, the skirt may be inverted. The elongated cannula may define a longitudinal axis, wherein when the skirt is in the first position, the inner surface may be radially closer to the longitudinal axis than the outer surface. When the skirt is in the second position, the outer surface may be radially closer to the longitudinal axis than the inner surface.

In aspects, the housing may include a seal assembly.

In aspects, the housing and the elongated cannula may define a central passage therethrough. The central passage may be configured to receive surgical instruments therethrough.

According to one aspect, a surgical assembly includes a trocar having a housing and an elongated cannula extending from the housing. The surgical assembly further includes a flexible skirt. The flexible skirt is secured to the elongated cannula. The flexible skirt has a first surface positioned to contact a tissue opening when the trocar is introduced into a body cavity. The flexible skirt has a second surface opposite to the first surface and positioned to contact the tissue opening when the trocar is removed from the body cavity.

In aspects, the first surface may support an antimicrobial material and the second surface may support a medical adhesive material. The medical adhesive material may include cyanoacrylate.

In aspects, the skirt may include a leading end portion and a trailing end portion. The leading end portion may be secured to the elongated cannula. The elongated cannula may extend to an insertion tip. The leading end portion of the skirt may be secured to the insertion tip. The trailing end portion of the skirt may be free.

In aspects, the skirt may be positioned to invert to enable the second surface to contact the tissue opening.

According to yet another aspect, a method for reducing wound infection with a trocar assembly is provided. The method includes inserting a skirt of a trocar assembly through a wound, coating the wound with antimicrobial material from the skirt, inverting the skirt, and coating the wound with a medical adhesive material from the skirt.

In aspects, coating the wound with the medical adhesive material may include coating the wound with cyanoacrylate from the skirt.

In aspects, coating the wound with the medical adhesive material may include sliding the inverted skirt along the wound when extracting the trocar assembly from the wound.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

DETAILED DESCRIPTION

Figure 1:
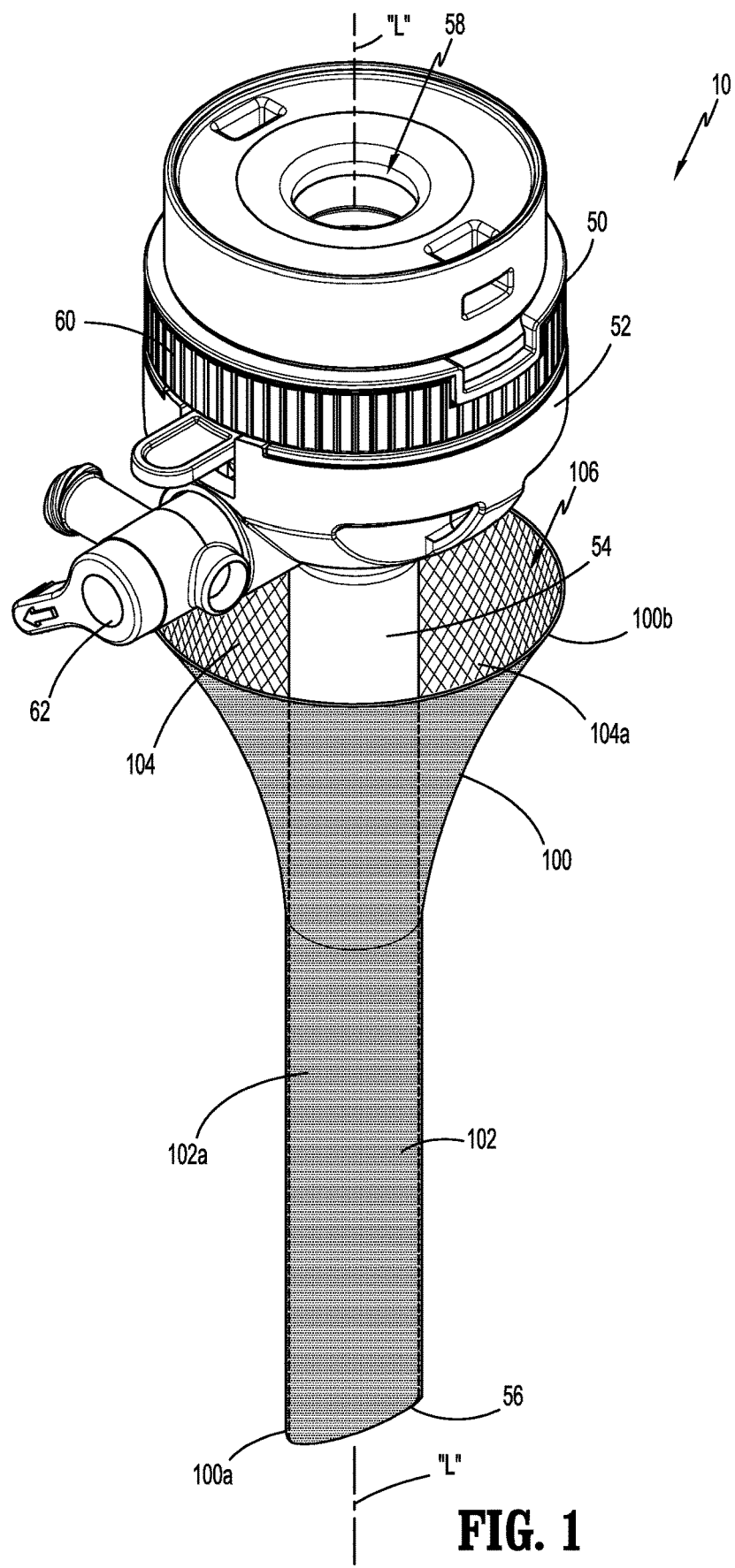
FIG. 1 is a perspective view of a trocar assembly in accordance with the principles of this disclosure.

Aspects of this disclosure are described in detail with reference to the drawings, in which like reference numerals designate identical or corresponding elements in each of the several views. Additionally, the term "proximal" or "trailing" refers to the portion of structure that is closer to the clinician and the term "distal" or "leading" refers to the portion of structure that is farther from the clinician. As commonly known, the term "clinician" refers to a doctor (e.g., a surgeon), a nurse, or any other care provider and may include support personnel.

In the following description, well-known functions or constructions are not described in detail to avoid obscuring this disclosure in unnecessary detail.

Figure 2:
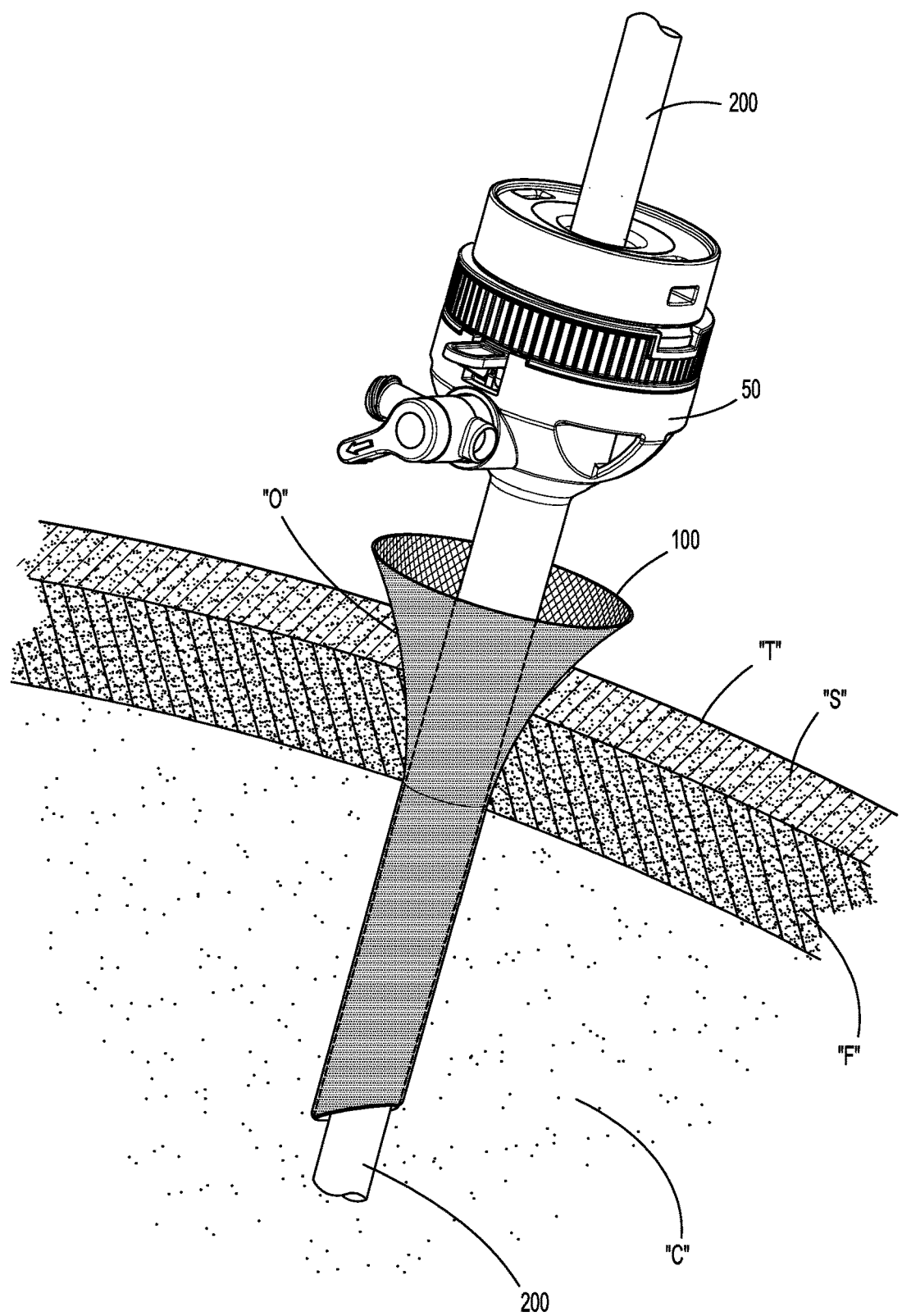
FIG. 2 is a perspective view of the trocar assembly of FIG. 1 illustrated introduced into a patient's body with a surgical instrument advanced therethrough.

With regard to FIGS. 1 and 2, a trocar assembly 10 includes a trocar 50 and skirt 100 secured to trocar 50. Trocar 50 is configured for insertion into a body cavity "C" (e.g., abdomen) through tissue "T" of a patient (e.g., skin "S" and fascia "F"). Trocar 50 includes a housing 52 supported on a trailing end portion thereof and an elongated cannula 54 that extends distally from housing 52 to an insertion tip 56 on a leading end portion of elongated cannula 54. Trocar 50 defines a longitudinal axis "L" and a central passage 58 that extends distally along longitudinal axis "L" from a trailing end portion of housing 52 through a leading end portion of insertion tip 56 of cannula 54 for receiving surgical instrumentation 200 therethrough (see FIG. 2). Such surgical instrumentation 200 can include graspers, forceps, staplers, endoscopes, clip appliers, stitching devices, etc. Housing 52 supports a seal assembly 60 within an inner cavity of housing 52. Seal assembly 60 of trocar 50 includes any number and/or type of seals for receiving surgical instrumentation 200 therethrough. Seal assembly 60 can include any number of disc seals, floating seals, and/or duckbill seals. Trocar 50 also includes an insufflation assembly 62 for selectively enabling insufflation fluid (e.g., saline) to be passed through trocar 50 to selectively insufflate the body cavity "C." For a more detailed description of similar trocars, one or more components of which may be incorporated into, or modified for use with trocar 50, reference can be made to, for example, U.S. Patent Application Publication No. 20150045623 and U.S. Pat. No. 8,070,730, the entire content of each of which is incorporated by reference herein.

Skirt 100 of trocar assembly 10 may be formed of any suitable flexible material, and may be a porous and/or non-porous structure such as a mesh, fibrous sheet, foam, film, and/or composite thereof. Indeed, skirt 100 may be fabricated from any biocompatible polymer that can be used in surgical procedures whether natural or synthetic. For example, skirt 100 may include, or be formed of, a material selected from polyethylene, polyurethanes, polyesters, polyethylene terephthalate, thermoplastic elastomers, thermoplastic vulcanizates, silicones, natural rubbers, styrene-butadiene-styrene block copolymers, or combinations thereof. Skirt 100 has a leading end portion 100a and a trailing end portion 100b. Leading end portion 100a of skirt 100 is secured to insertion tip 56 of elongated cannula 54 and extends proximally along elongated cannula 54 to trailing end portion 100b of skirt 100. Skirt 100 may extend partially and/or completely along the length of elongated cannula 54. In this regard, skirt 100 may be positioned to protect against microbials not only on the skin surface, but along elongated cannula 54 so that such microbials do not migrate into an open wound (e.g., incision). Skirt 100 may be proportionally sized to a diameter of trocar 50 to ensure adequate coverage without excessive bunching around elongated cannula 54, limiting swelling around an incision site. Trailing end portion 100b of skirt 100 may flare radially outward to a trailing end of trailing end portion 100b. Skirt 100 includes an outer surface 102 and an inner surface 104 that defines a central opening 106 for receiving elongated cannula 54 therein. Skirt 100 is flexible supported on elongated cannula 54 and is positioned to invert in response to an application of distal force applied thereto. Outer and/or inner surfaces 102, 104 may include one or more biocompatible materials and/or agents (e.g., bioactive) that can be partially and/or wholly, impregnated, layered, and/or coated thereon and/or otherwise retained therein. For example, outer surface 102 of skirt 102 includes an antimicrobial material 102a such as silver benzoate and inner surface 104 includes a medical adhesive material 104a (e.g., a dermal glue) such as cyanoacrylate, silicone, and/or polyurethane. These materials may be synthetic and/or biological/natural.

As used herein, the term "bioactive agent" includes "active therapeutic agent" (ATA) and can be used interchangeably. In its broadest sense, the term "bioactive agent" includes any substance or mixture of substances that have clinical use. The bioactive agents may invoke a biological action, exert a biological effect, or play a role in one or more biological processes. Consequently, bioactive agents may or may not have pharmacological activity per se, e.g., a dye, or fragrance. Alternatively, a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. The bioactive agent may be applied to the disclosed structure in any suitable form of matter, e.g., films, powders, liquids, gels, and the like. The type and amount of bioactive agent(s) used will depend, among other factors, on the particular site and condition to be treated.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

In some aspects, the bioactive agent may be a growth factor, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. In some aspects, members of the transforming growth factor (TGF) supergene family, which are multifunctional regulatory proteins, are utilized. Members of the TGF supergene family include the beta transforming growth factors (for example, TGF-$\beta$1, TGF-$\beta$2, TGF-$\beta$3); bone morphogenetic proteins (for example, BMP-1, BMP-2, BMP-3MP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Vascular growth factor (VGF) can be important to reestablishing blood supply to surrounding tissue.

In some aspects, the bioactive agent is a biologic or cell specific ligand capable of attracting or recruiting specific cell types, such as smooth muscle cells, stem cells, immune cells, and the like.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins, such as vitamin A, B-12, C, D, combinations thereof, and the like; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include biologics and protein therapeutics, such as, viruses, bacteria, lipids, amino acids, cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons ($\beta$-IFN, $\alpha$-IFN, and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Suitable antimicrobial agents include, for example, triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in a bioactive coating of this disclosure.

Figure 3:
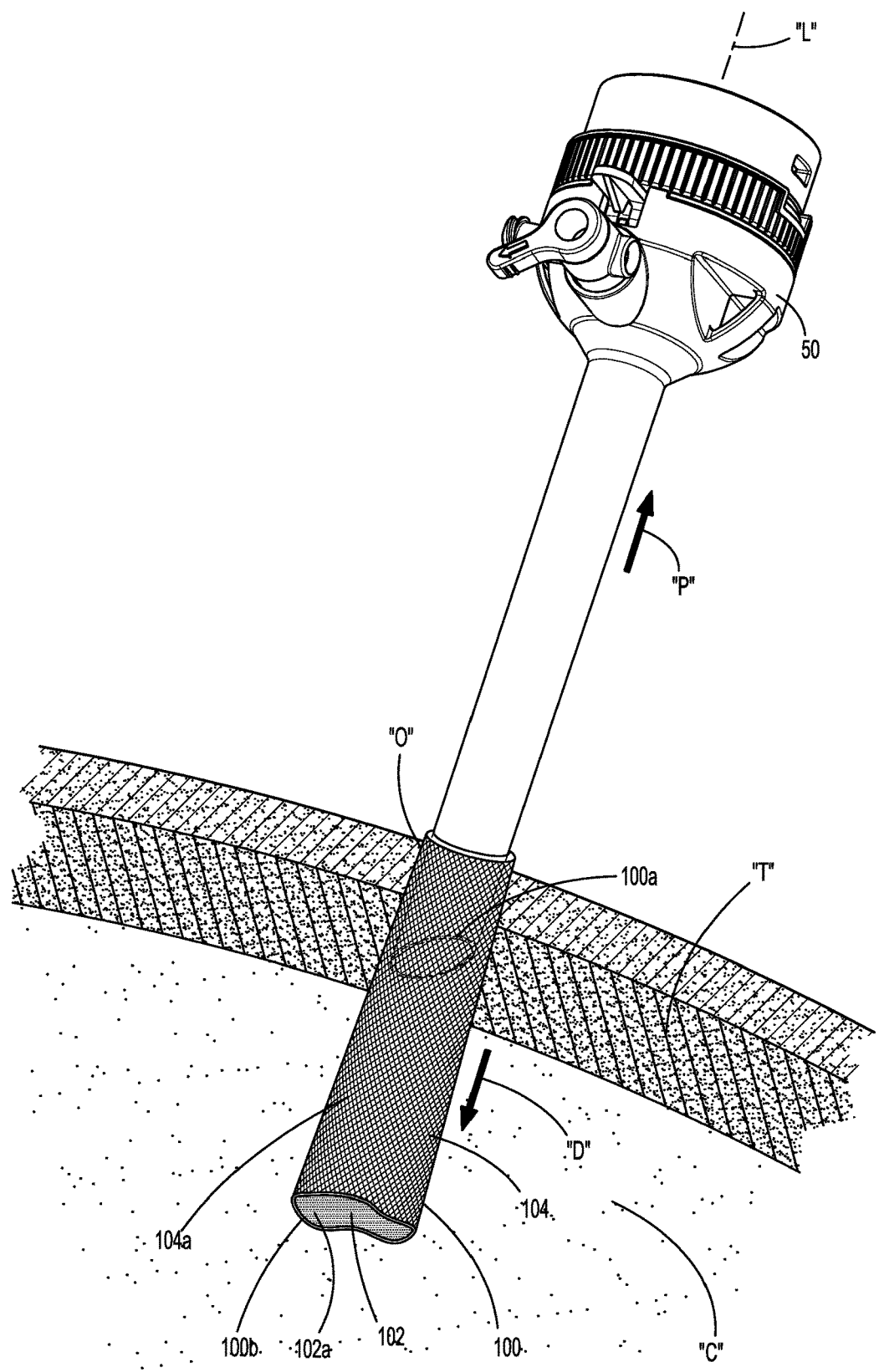
FIGS. 3 and 4 are progressive views illustrating the trocar assembly being removed from the patient's body.
Figure 4:
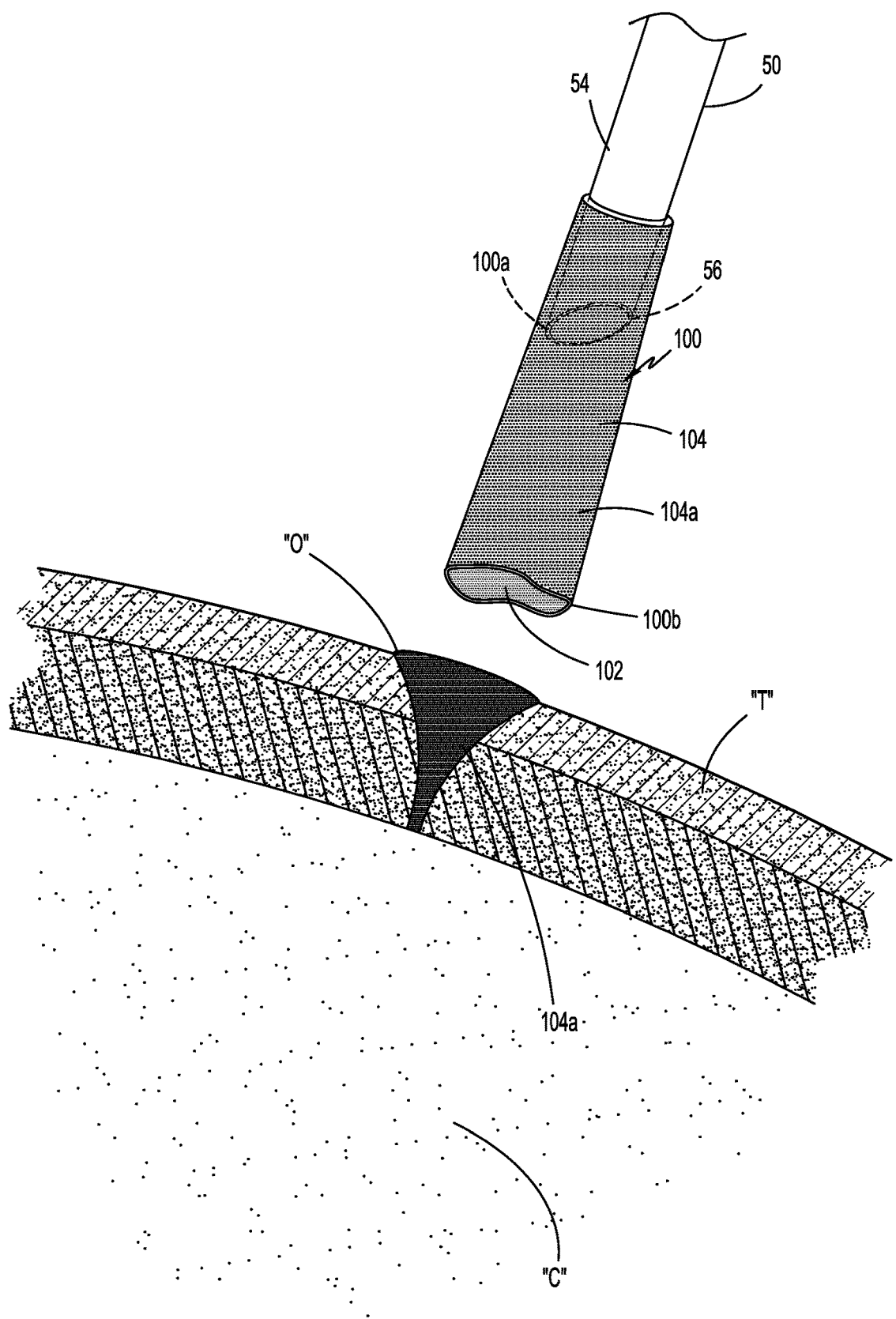

With reference to FIGS. 1-4, in use, trocar assembly 10 is inserted through an opening "O" in tissue "T", which may be a natural or artificial opening (e.g., an incision) so that antimicrobial material 102a along outer surface 102 of skirt 102 contacts the tissue "T" surrounding the opening "O," as seen in FIG. 2, to create a sterile barrier along the surfaces of the opening "O." With trocar assembly 10 inserted in the tissue "T," one or more surgical instruments 200 can be introduced into the body cavity "C" through trocar assembly 10 for accessing a surgical site. As seen in FIG. 3, trocar assembly 10 can be removed, for example, upon completion of a surgical procedure. Trocar 50 can be advanced distally towards body cavity "C" and sufficiently deep to cause skirt 100 to invert (e.g., where trailing end portion 100b advances distally toward body cavity "C," as indicated by arrow "D," so that trailing end portion 100b advances through or nearly through opening "O"). With skirt 100 disposed in an inverted position (FIG. 3) inner surface 104 of skirt 100 is disposed in an outer position (e.g., radially farther from longitudinal axis "L") and outer surface 102 of skirt 100 is disposed in an inner position (e.g., radially closer to longitudinal axis "L"). In this inverted position of skirt 100, the medical adhesive material 104a (e.g., cyanoacrylate) contacts the tissue "T" surrounding the opening "O" as trocar assembly 10 is withdrawn proximally through opening "O," as indicated by arrow "P," so that the medical adhesive material 104a coats the tissue "T" surrounding the opening "O" and seals off the dermal layers of the tissue "T," reducing any need for a suture close. Advantageously, materials such as cyanoacrylate also have anti-microbial properties, which can protect wounds (e.g., the incision) from infections. The disclosed subject matter may benefit, in particular, patients who have problems with wound healing; for example, patients who may be diabetic or obese. In one specific example, such subject matter may particularly benefit patients with diabetes mellitus whose wounds tend to heal slowly and who are prone to contracting infection.

The various trocars disclosed herein may also be configured for use with robotic surgical systems, and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

For a more detailed description of similar trocars, one or more components of which can be included with, or modified for use with, the disclosed structure, reference can be made to U.S. Pat. No. 5,807,338, filed Oct. 20, 1995 and U.S. Pat. No. 5,603,702, filed on Aug. 8, 1994, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular aspects. It is to be understood, therefore, that this disclosure is not limited to the precise aspects described, and that various other changes and modifications may be effected by one skilled in the art without departing from the scope or spirit of this disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A trocar assembly comprising:
   a housing;
   an elongated cannula extending from the housing to an insertion tip; and
   a skirt having a leading end portion and a trailing end portion, the leading end portion secured to the insertion tip, the skirt having an outer surface supporting an antimicrobial material and an inner surface supporting a medical adhesive material.

2. The trocar assembly of claim 1, wherein the medical adhesive material includes cyanoacrylate.

3. The trocar assembly of claim 1, wherein the skirt is flexible.

4. The trocar assembly of claim 1, wherein the trailing end portion of the skirt is a free end.

5. The trocar assembly of claim 1, wherein the skirt is positioned to move between a first position and a second position.

6. The trocar assembly of claim 5, wherein in the second position, the skirt is inverted.

7. The trocar assembly of claim 5, wherein the elongated cannula defines a longitudinal axis, and wherein when the skirt is in the first position, the inner surface is radially closer to the longitudinal axis than the outer surface.

8. The trocar assembly of claim 7, wherein when the skirt is in the second position, the outer surface is radially closer to the longitudinal axis than the inner surface.

9. The trocar assembly of claim 1, wherein the housing includes a seal assembly.

10. The trocar assembly of claim 1, wherein the housing and the elongated cannula define a central passage therethrough, the central passage configured to receive surgical instruments therethrough.

11. A surgical assembly comprising:
    a trocar having a housing and an elongated cannula extending from the housing; and
    a flexible skirt secured to the elongated cannula, the flexible skirt having a first surface positioned to contact a tissue opening when the trocar is introduced into a body cavity, the flexible skirt having a second surface opposite to the first surface and positioned to contact the tissue opening when the trocar is removed from the body cavity.

12. The surgical assembly of claim 11, wherein the first surface supports an antimicrobial material and the second surface supports a medical adhesive material.

13. The surgical assembly of claim 12, wherein the medical adhesive material includes cyanoacrylate.

14. The surgical assembly of claim 11, wherein the flexible skirt includes a leading end portion and a trailing end portion, the leading end portion secured to the elongated cannula.

15. The surgical assembly of claim 14, wherein the elongated cannula extends to an insertion tip, and wherein the leading end portion of the flexible skirt is secured to the insertion tip.

16. The surgical assembly of claim 15, wherein the trailing end portion of the flexible skirt is free.

17. The surgical assembly of claim 11, wherein the flexible skirt is positioned to invert to enable the second surface to contact the tissue opening.

18. A method for reducing wound infection with a trocar assembly, the method comprising:
    inserting a skirt of a trocar assembly through a wound;
    coating the wound with antimicrobial material from the skirt;
    inverting the skirt; and
    coating the wound with a medical adhesive material from the skirt.

19. The method of claim 18, wherein coating the wound with the medical adhesive material includes coating the wound with cyanoacrylate from the skirt.

20. The method of claim 18, wherein coating the wound with the medical adhesive material includes sliding the inverted skirt along the wound when extracting the trocar assembly from the wound.

* * * * *